United States Patent [19]

Azumendi

[11] Patent Number: 5,705,607

[45] Date of Patent: Jan. 6, 1998

[54] PROCEDURES FOR THE ISOLATION AND TITRATION OF SARCOCYSTINE OR PARASITE TOXIN OF SARCOCYSTIS GENUS

[76] Inventor: Jose Luis Azumendi, Calle 70 A No. 11-43, Apartado 28712, Santafe De Bogota, Colombia

[21] Appl. No.: 695,745

[22] Filed: Jul. 12, 1996

[30] Foreign Application Priority Data

Feb. 16, 1996 [GB] United Kingdom ............. 9603304

[51] Int. Cl.⁶ .................. A61K 38/00; A61K 31/12; C07K 14/00
[52] U.S. Cl. .................. 530/331; 530/333; 530/380; 514/12; 424/531
[58] Field of Search .................. 424/531; 530/380; 514/12

[56] References Cited

U.S. PATENT DOCUMENTS 3,998,947 12/1976 D'Hinterland .................. 514/12
5,023,260 6/1991 Lindner et al. .................. 514/269

*Primary Examiner*—Cecilia J. Tsang
*Assistant Examiner*—P. Lynn Touzeau
*Attorney, Agent, or Firm*—J. Sanchelima

[57] ABSTRACT

The present invention provides the technique for isolating the toxin of the Sarcocystis protozoa, which may be later used in the production of specific antibodies against the sarcocystine responsible for the symptoms of sarcocystosis. The technique of the invention consists of separating the blood serum of an infected animal followed by dialysis thereof and finally the sample is dried. The technique is more effective when heart muscle material from an intermediate host with Sarcocystis cysts is used to contaminate a carnivorous mammal final host.

10 Claims, No Drawings

PROCEDURES FOR THE ISOLATION AND TITRATION OF SARCOCYSTINE OR PARASITE TOXIN OF SARCOCYSTIS GENUS

II. BACKGROUND OF THE INVENTION

1. Field of the Invention

This invention relates to a procedural technique for the isolation and titration of the toxin sarcocystine which is produced by a parasite of the Sarcocystis genus of protozoa. This toxin may then be used in the production of toxides or vaccines and also in the production of specific antibodies against the toxin.

More particularly, the present invention relates to a step by step procedural technique for isolating the toxin produced by a parasite of the Sarcocystis genus. In particular, material, preferably heart muscle, from an animal Intermediate Host (IH) with Sarcocystis cysts is used to contaminate a Final Host (FH). After the development of the disease in the Final Host, a percentage of its blood is extracted and by means of a centrifugation process the serum is separated, then dialysed, preferably by passing through a sterile Physiological Saline Solution (PSS), and it is finally held for storage at a specific temperature.

2. Description of the Related Art

One of the current known methods for isolating the toxin includes developing the toxin in macrocysts in sheep contaminated with the parasite. According to this method, the macrocysts which are formed in the oesophagus of the sheep can reach a visible size and contain relatively high quantities of toxin. Such a method entails the inconvenience that the animal must be sacrificed to obtain a few millimeters of pure toxin. By contrast the animal is kept alive and in good living conditions according to the technique of the present invention, so becoming a good toxin donor from which a substantial volume thereof may be extracted regularly for a long time.

In an alternative known method, cell cultures may be utilized as supports for in vitro cultures of Sarcocystis, which allows for a totally-controlled environment to be maintained. The inconvenience arises from the fact that the parasite only begins to produce the toxin 30 or more days after inoculation and then production ends shortly thereafter. Maintenance of these cultures for a long time becomes expensive and they yield a supernatant compound as complex as the animal's blood serum. This latter problem can be overcome using a purification procedure of the present invention.

The evidence of the infection with the parasite, known as Sarcocystis in man, is usually an accidental finding in the course of histopathological examinations. Protozoa of the Sarcocystis genus behave like an enzoonosis, and it has been reported all over the world that they are a causal agent of many pathologies in man. This parasite mainly affects lower strata people with deficient nutrition although any person may be susceptible to it.

Protozoa of the Sarcocystis genus were reported for the first time in 1843 when a researcher by the name of Miescher found tubules in the skeletal muscle of a house mouse. Doctors Rommel and Heidorn in 1972 found that the protozoa's life cycle was heterogeneous, with the asexual phase in the prey, the intermediate host, and the sexual phase in the pillager, the final host. At present, 122 species of the protozoa have been identified and in 56 of these two hosts are known. From the zoonosis point of view, those developing the asexual phase in humans are interesting, the final hosts of which are unknown to date, and the two which develop the sexual phase in humans which are known.

Considering all scientific knowledge at the world level concerning multiple sclerosis, lateral and amyotrophic sclerosis and the syndrome of chronic fatigue, there is no report of any link between a Sarcocystis-like protozoa and these diseases. According to a review of the literature in the past months, we have found that multiple sclerosis is considered to be closely linked to alterations in the immune system, mainly with alterations of the Tcd 4 lymphocytes.

Notwithstanding what has been expressed previously we have found that infection due to Sarcocystis gives rise to symptoms such as muscle spasms, intermittent diarrhoea and chronic fatigue, even to multiple sclerosis. In our research, it has been determined that the pathogeny of this organism is caused by the toxin from Sarcocystis genus. It is desirable for this toxin to be isolated so as to be inactivated but in such a way that it preserves its antigenic capacity, in order to obtain a specific immune-inducted response from the part of the molecule immunologically responsive to a vaccine based on this toxin.

V. DETAILED DESCRIPTION OF THE PREFERRED EMBODIMENT

The present invention provides the technique for isolating protozoa sarcocystine, i.e., the toxin of the Sarcocystis protozoa, which may be later used in the production of specific antibodies against the sarcocystine responsible for the symptoms of sarcocystosis.

In accordance with the present invention there is provided a method of isolating a sarcocystine toxin from a mammal including the steps of:

(a) dialyze blood serum from a mammal contaminated with the sarcocystine parasite against an aqueous salt solution; and (b) drying the dialysed solution to isolate purified sarcocystine toxin.

It is preferred that a mammal be used as an FH, e.g., a carnivore such as a canine animal. When an FH is used, it is also preferred that the mammal is infected with Sarcocystis parasite by muscle, and especially cardiac muscle, containing Sarcocystis cysts. It is particularly preferred that the dialysis solution consists of about 9 gm per liter of sodium chloride, although any salt solution of equivalent osmotic pressure can also be used.

Preferably a mammal is used as an Intermediate Host, wherein the Intermediate Host is a herbivore, and wherein the Intermediate Host is infected with sporozoites from the stools of the Final Host. Desirably the contaminated mammal has an absolute lymphocyte count at least 20% higher than its pre-contamination count.

The invention also relates to the determination of the optimum time for bleeding the donor as explained herein below. This involves the use of the toxicogenic characteristics of sarcocystine. By using the technique of the present invention, it is possible to determine a 98.4% specificity (which means that examination of 100 patients positive to the toxin shows that 98 of them are detected by the test) and 99.00% sensitivity (which means that, upon examination of 100 patients negative to the toxin, 99 of them are detected by the test), and it may be confirmed through biological titration. The toxin can be titrated in biological tests with a specificity of 99.80% (which means that upon examining 100 patients positive to the toxin, 100 of them are detected by the test), and a sensitivity of 99.99% (which means that upon examining 100 patients negative to the toxin, 100 of them are detected by the test).

The present invention also relates to the desiccation of the toxin isolated by dialysis in order to stabilize it for storage purposes.

In a preferred technique, an FH (e.g., a canine animal), of which the absolute number of pre-infection lymphocytes is known, is contaminated with heart muscle of an IH (e.g. a herbivore such as a bovine animal) containing Sarcocystis cysts. It is preferred that the heart muscle does not contain any other aetiological agent. Following this contamination of the FH, it is expected that such FH will develop Sarcocystosis. The absolute lymphocytes count of the FH is an indication of when the next step in the procedure can occur. Once the lymphocyte count reaches a minimum of 20% above the pre-contamination count, biological titration of the toxin, as described herein below, can be applied to obtain a minimum titrate of 3 units. At this point blood may be obtained from the FH. This is likely to occur between 50 and 80 days after contamination. The absolute lymphocyte count of the FH is an indicator of the toxin concentration due to the mitogenic capacity of sarcocystine. Sarcocystine is highly specific with respect to lymphocytes B, a feature not found in other substances from the blood of a mammal.

The FH is bled to obtain the required blood which is collected in a siliconed 500 milliliter sterile Erlenmeyer flask without anticoagulant. The serum is then separated at 800 g for 20 minutes in sterile centrifuge tubes in order to eliminate the corpuscular blood components. The presence of a small degree of haemolysis is acceptable. The serum is then dialysed against a sterile PSS composed of about 9 grams of sodium chloride in 1000 cubic centimeters of distilled water for 36 to 48 hours, keeping the temperature between 18 and 25 degrees centigrade and shaking continuously.

At this point in the process, the toxin is isolated in the PSS with a minimum purity of 80%. Due to the size of the toxin molecule which is being isolated, temperature and dialysis time, it is possible to eliminate all those molecules which may cause alterations in the toxin usage.

The dialyzed solution is then dried at a temperature of 37° C. in order to remove the water and obtain the toxin concentrate. The dried toxin is then stored in sterile amber flasks and they are kept at room temperature in a dry place.

The remaining contaminants located in the desiccated portion of the dialysis are glucose and some minerals, none of which affect the toxicogenic, physical and/or biochemical characteristics of sarcocystine.

This procedure results in the isolation of a molecule behaving like hystamine which must be examined in order to determine the toxicogenic titrate which is found. It is important to make this titration since epitopes, that is to say, the part of the molecule which is toxicologically active, is the same part of the molecule which is immunologically responsive to both humoral and cellular defenses. Thus, a strain of the parasite which has proven production of very toxicogenic metabolites must be selected.

To select such a strain, the IH from which the strain is to be obtained must come from an area where the chronic sarcosporidiosis is frequent and with very severe symptoms of the chronic disease demonstrated by between 10,000 and 30,000 bradozoids per gram of wide dorsal muscle. It must also be verified through serological tests that the animal does not suffer from any other disease.

When the muscle which will be used to contaminate the FH is administered, sterile technique should be used. Utilization of the cardiac muscle is recommended.

With this selected muscle, 4 to 10 FH young adults can be contaminated. These FH must show general vascular lesions and intermittent diarrhoea and that lymphocyte counts must exceed a minimum of 20% above the pre-contamination count.

Once these steps have been carried out and the titration of the toxin (as described below) shows the titrate to be greater than or equal to 4 units, the conditions are suitable for the collection and purification of the toxin.

When high toxin volumes are required, the procedure should be applied to larger size mammals (e.g., equine and bovine animals) with slight variations. A stool sample of previously contaminated FH, which has developed the whole picture described above, is taken and the sporozoites contained in the sample are purified. This is done by dissolving the stool sample in over-saturated glucose solution at the proportion of 1 volume of stool per 3 volumes of over-saturated solution, the uppermost part of the preparation is collected, it is diluted in PSS and centrifuged at 300 g for 10 minutes, the supernatant is discarded and the bottom residue is re-suspended in PSS to perform the toxin count.

The IH is contaminated with the parasite so prepared at a dosage of 700 sporozoites per kilogram. After 90 days, the IH is found in the chronic phase of the disease with high toxin contents in its blood, which makes it useful for extraction of the toxin. In order to confirm the concentration of the toxin, the same techniques as described above may apply to the FH, i.e., lymphocyte count and/or biological titration of the toxin.

Between 40 and 60 days after contamination, the IH may show some symptoms of the severe disease, which may be treated symptomatically but no medicines for killing the Sarcocystis are to be used.

Titration Procedure

Three groups of 5 to 10 20-gram mice are selected. The toxin is diluted with PSS at two known concentrations, between 0.5 and 1 mg per ml. The first group of mice are orally administered with 0.2 ml of the toxin at dilution 1, the second group of mice are orally administered with 0.2 ml. of the toxin at dilution 2, and the third group is used as a control and receives 0.2 ml. of PSS without the toxin.

Eighteen hours later blood is obtained from all mice to make a total count of lymphocytes. They are then sacrificed to perform a necropsy.

In the event that the administration of the toxin has been successful, the mice that received the toxin must present haemoperitoneum among other hemorrhages, while the control animals do not present any hemorrhage at all. Furthermore, the average of the total counts of lymphocytes in the inoculated animals will be higher than the average of the total counts of lymphocytes of the control animals.

An estimate of the toxin units ("U") is calculated according to the following formula:

$$U/mg = \frac{(Y\,lri - Y\,lrni) \cdot 50 \cdot d}{Y\,lrni}$$

Where:
  Y lri=The average of the total lymphocytes count in the inoculated animals;
  Y lrni=The average of the total lymphocyte counts in the non-inoculated animals;
  d=Dilution factor in which the toxin was prepared.

A Sarcocystis type toxin unit is the amount of this toxin needed to increase by 10% the average of the total lymphocyte count of the contaminated mice as compared to the non-contaminated mice.

What is claimed is:

1. A method of isolating a Sarcocystine toxin from a mammal contaminated with the Sarcocystine parasite including the steps of:
   A) dialyze blood serum from a mammal contaminated with the Sarcocystine parasite against an aqueous salt solution; and
   B) drying the dialysed solution to isolate purified Sarcocystine toxin.

2. A method as claimed in claim 1 wherein the contaminated mammal is a Final Host and is a carnivore.

3. A method as claimed in claim 2 wherein a mammal is used as an Intermediate Host.

4. A method as claimed in claim 3 wherein the Intermediate Host is a herbivore.

5. A method as claimed in claim 3 wherein the Intermediate Host is infected with sporozoites from the stools of the Final Host.

6. A method as claimed in claim 5 wherein the contaminated mammal is contaminated with muscle containing Sarcocystis cysts.

7. A method as claimed in claim 6 wherein the contaminated mammal has an absolute lymphocyte count at least 20% higher than its pre-contamination count.

8. A method as claimed in claim 7 wherein the dialysis solution consists of about 9 grams per liter of sodium chloride.

9. A method as claimed in claim 8 wherein the dialysis step is carried out for 36 to 48 hours.

10. A method as claimed in claim 9 wherein the dialysis step is carried out at a temperature between 18 and 25 degrees centigrade.

* * * * *